(12) United States Patent
Wastlund-Karlsson et al.

(10) Patent No.: US 8,052,665 B2
(45) Date of Patent: Nov. 8, 2011

(54) ABSORBENT ARTICLE COMPRISING AN ELASTIC LAMINATE

(75) Inventors: Jan Wastlund-Karlsson, Molndal (SE); Margareta Wennerback, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 136 days.

(21) Appl. No.: 11/630,372

(22) PCT Filed: Jun. 22, 2004

(86) PCT No.: PCT/SE2004/001004
§ 371 (c)(1),
(2), (4) Date: Dec. 21, 2006

(87) PCT Pub. No.: WO2005/122984
PCT Pub. Date: Dec. 29, 2005

(65) Prior Publication Data
US 2008/0033387 A1    Feb. 7, 2008

(51) Int. Cl.
*A61F 13/15* (2006.01)
(52) U.S. Cl. ........... 604/385.22; 604/385.3; 604/385.31; 604/385.29
(58) Field of Classification Search .............. 604/385.22, 604/385.28–385.31
See application file for complete search history.

(56) References Cited

U.S. PATENT DOCUMENTS 3,424,162 A    1/1969 Parravicini
(Continued)

FOREIGN PATENT DOCUMENTS

CO    2007-003796 A    1/2007
(Continued)

OTHER PUBLICATIONS

Sueo Kawabata, "The Standardization and Analysis of Hand Evaluation", Second Edition, The Hand Evaluation and Standardization Committee, The Textile Machinery Society of Japan, published by The Textile Machinery Society of Japan, Osaka, Japan, Jul. 1980.
International Search Report dated Feb. 10, 2005.
Hildeberg et al., Copending U.S. Appl. No. 11/630,371, filed Dec. 21, 2006 entitled "Absorbent Article Comprising an Elastic Laminate".

(Continued)

*Primary Examiner* — Loan Thanh
*Assistant Examiner* — Lynne Anderson
(74) *Attorney, Agent, or Firm* — Buchanan Ingersoll & Rooney PC

(57) ABSTRACT

A pant type absorbent article such as a pant diaper, a sanitary pant or incontinence pant, the article having a core region including an absorbent core and a chassis region surrounding the core region. The article at least in part of the chassis region has an outer coversheet in the form of an elastic laminate having a Softness (S) according to Kawabata of at least 20. The laminate includes first and second layers of fibrous material and an elastic film layer located between the first and second fibrous layers.

24 Claims, 2 Drawing Sheets

U.S. PATENT DOCUMENTS

| | | |
|---|---|---|
| 4,119,450 A | 10/1978 | Bianco |
| 4,663,220 A | 5/1987 | Wisneski et al. |
| 4,698,261 A | 10/1987 | Bothe et al. |
| 4,739,012 A | 4/1988 | Hagman |
| 4,777,080 A | 10/1988 | Harris, Jr. et al. |
| 4,842,596 A | 6/1989 | Kielpikowski et al. |
| 4,932,949 A | 6/1990 | Thygesen et al. |
| 4,965,122 A * | 10/1990 | Morman .................. 442/328 |
| 5,114,781 A | 5/1992 | Morman |
| 5,143,679 A | 9/1992 | Weber et al. |
| 5,156,793 A | 10/1992 | Buell et al. |
| 5,167,897 A | 12/1992 | Weber et al. |
| 5,261,899 A | 11/1993 | Visscher et al. |
| 5,336,545 A * | 8/1994 | Morman .................. 428/152 |
| 5,422,172 A | 6/1995 | Wu |
| 5,440,764 A | 8/1995 | Matsushita |
| 5,462,541 A | 10/1995 | Bruemmer et al. |
| 5,514,470 A | 5/1996 | Haffner et al. |
| 5,592,690 A | 1/1997 | Wu |
| 5,628,738 A | 5/1997 | Suekane |
| 5,634,216 A | 6/1997 | Wu |
| 5,635,290 A | 6/1997 | Stopper et al. |
| 5,706,524 A | 1/1998 | Herrin et al. |
| 5,733,628 A | 3/1998 | Pelkie |
| 5,746,730 A | 5/1998 | Suzuki et al. |
| 5,769,838 A | 6/1998 | Buell et al. |
| 5,861,074 A | 1/1999 | Wu |
| 5,921,973 A | 7/1999 | Newkirk et al. |
| 6,072,005 A | 6/2000 | Kobylivker et al. |
| 6,106,925 A | 8/2000 | Palumbo |
| 6,210,386 B1 * | 4/2001 | Inoue .................. 604/385.13 |
| 6,240,569 B1 | 6/2001 | van Gompel et al. |
| 6,476,289 B1 | 11/2002 | Buell et al. |
| 6,540,731 B2 | 4/2003 | Magnussson et al. |
| 6,552,245 B1 | 4/2003 | Roessler et al. |
| 6,585,713 B1 | 7/2003 | LeMahieu et al. |
| 6,627,564 B1 | 9/2003 | Morman et al. |
| 6,914,018 B1 | 7/2005 | Uitenbroek et al. |
| 7,722,591 B2 | 5/2010 | Back |
| 2002/0002021 A1 | 1/2002 | May et al. |
| 2002/0019187 A1 | 2/2002 | Carroll et al. |
| 2002/0029026 A1 | 3/2002 | Furuya et al. |
| 2002/0052591 A1 | 5/2002 | Zehner et al. |
| 2003/0022582 A1 | 1/2003 | Cree et al. |
| 2003/0078558 A1 | 4/2003 | Karami et al. |
| 2004/0078018 A1 | 4/2004 | Van Gompel et al. |
| 2004/0102746 A1 | 5/2004 | Mortell et al. |
| 2004/0116887 A1* | 6/2004 | Thorson et al. .......... 604/385.22 |
| 2004/0122405 A1 | 6/2004 | Van Gompel et al. |
| 2004/0122406 A1* | 6/2004 | Moser et al. ............. 604/385.22 |
| 2004/0127878 A1 | 7/2004 | Olson et al. |
| 2004/0133180 A1 | 7/2004 | Mori et al. |
| 2004/0192140 A1 | 9/2004 | Schneider et al. |
| 2004/0197588 A1 | 10/2004 | Thomas et al. |
| 2004/0241389 A1 | 12/2004 | Chung et al. |
| 2004/0243086 A1* | 12/2004 | VanGompel et al. ...... 604/385.3 |
| 2005/0010186 A1 | 1/2005 | Otsubo et al. |
| 2005/0101216 A1 | 5/2005 | Middlesworth et al. |
| 2005/0106980 A1 | 5/2005 | Abed et al. |
| 2006/0148358 A1 | 7/2006 | Hall et al. |
| 2007/0233034 A1 | 10/2007 | Hildeberg et al. |
| 2008/0000003 A1 | 1/2008 | Melander |
| 2008/0033387 A1 | 2/2008 | Wastlund-Karlsson et al. |
| 2009/0306616 A1 | 12/2009 | Wennerback |
| 2010/0036355 A1 | 2/2010 | Hakansson et al. |

FOREIGN PATENT DOCUMENTS

| | | |
|---|---|---|
| EP | 0 287 388 | 10/1988 |
| EP | 0 304 957 A2 | 3/1989 |
| EP | 0 360 929 A1 | 4/1990 |
| EP | 0 409 307 | 1/1991 |
| EP | 0 418 493 | 3/1991 |
| EP | 0 486 006 | 5/1992 |
| EP | 0 605 012 | 7/1994 |
| EP | 0 861 647 A2 | 9/1998 |
| EP | 0 714 351 B1 | 12/1998 |
| EP | 0 604 731 B1 | 6/1999 |
| EP | 1 035 818 B1 | 9/2000 |
| EP | 1 184 022 | 3/2002 |
| EP | 1 384 459 A2 | 7/2003 |
| EP | 1 473 008 | 11/2004 |
| FR | 2 586 558 | 3/1987 |
| FR | 2 810 879 | 1/2002 |
| GB | 2 284 538 A | 6/1995 |
| JP | 06255006 A | 9/1994 |
| JP | 07-252762 | 10/1995 |
| JP | 9-286085 | 11/1997 |
| JP | 10-043235 A | 2/1998 |
| JP | 2002 058 703 | 2/2002 |
| JP | 2002-065740 | 3/2002 |
| JP | 2002-172137 A | 6/2002 |
| JP | 2002-520090 T | 7/2002 |
| JP | 2002-273808 | 9/2002 |
| JP | 2003-520146 | 7/2003 |
| JP | 2003-290284 | 10/2003 |
| JP | 2004-050621 | 2/2004 |
| JP | 2004-098356 | 4/2004 |
| JP | 2004-519270 | 7/2004 |
| RU | 2 008 774 | 3/1994 |
| RU | 2 221 531 | 1/2004 |
| SU | 965339 A | 10/1982 |
| TW | 233473 | 11/1994 |
| WO | WO 95/19258 | 7/1995 |
| WO | WO 96/10979 A1 | 4/1996 |
| WO | WO 97/29722 A1 | 8/1997 |
| WO | 97/34037 | 9/1997 |
| WO | 98/37847 | 9/1998 |
| WO | WO 03/019714 A1 | 3/1999 |
| WO | WO 99/27876 A1 | 6/1999 |
| WO | WO 99/32164 A1 | 7/1999 |
| WO | WO 00/02511 A1 | 1/2000 |
| WO | WO 00/45764 A1 | 8/2000 |
| WO | WO 01/30563 A1 | 5/2001 |
| WO | WO 01/45927 A1 | 6/2001 |
| WO | WO 01/53076 | 7/2001 |
| WO | WO 2005/122984 A1 | 4/2002 |
| WO | WO 2005/122985 A1 | 4/2002 |
| WO | WO 02/34185 | 5/2002 |
| WO | WO 02/49560 A1 | 6/2002 |
| WO | WO 03/004748 A1 | 1/2003 |
| WO | 03/047488 A1 | 6/2003 |
| WO | WO 2004/058120 | 7/2004 |
| WO | WO 2004/060251 A1 | 7/2004 |
| WO | WO 2004/078083 A1 | 9/2004 |
| WO | WO 2005/095700 A1 | 10/2005 |
| WO | WO 2006/038837 A1 | 4/2006 |
| WO | WO 2006/093443 A1 | 4/2006 |
| WO | WO 2006/093439 A1 | 9/2006 |
| WO | WO 2006/093440 A1 | 9/2006 |
| WO | WO 2007/114744 A1 | 10/2007 |
| WO | WO 2008/060194 A1 | 5/2008 |

OTHER PUBLICATIONS

Karlson et al., Copending U.S. Appl. No. 11/576,497, filed Dec. 3, 2008 entitled "Absorbent Article Comprising an Elastic Web Material".

Melander Copending U.S. Appl. No. 11/845,153, filed Aug. 27, 2007 entitled "Underwear Article Comprising an Elastic Laminate".

Wennerback, Copending U.S. Appl. No. 12/446,297, filed Apr. 20, 2009 entitled "Absorbent Article Comprising an Elastic Laminate".

Norby et al., Copending U.S. Appl. No. 12/477,694, filed Apr. 29, 2009 entitled "Elastic Laminate and Absorbent Article Comprising the Laminate".

Wennerback, Copending U.S. Appl. No. 12/514,086, filed May 8, 2009 entitled "Absorbent Article Comprising an Elastic Laminate Material".

Non-Final Office Action in Copending U.S. Appl. No. 11/630,371 to Hildeberg et al. dated Oct. 5, 2009.

An English Translation of the Office Action dated Jan. 4, 2011, issued in corresponding Japanese Patent Application No. 2007-517993.

An English Translation of the Notice of Reasons for Rejection issued in the corresponding Japanese Patent Application No. 2007-517994 dated Nov. 24, 2009.

* cited by examiner

ABSORBENT ARTICLE COMPRISING AN ELASTIC LAMINATE

FIELD OF THE INVENTION

The present invention is directed to a pant type absorbent article such as a pant diaper, a sanitary pant or incontinence garment, said article having a core region comprising an absorbent core and a chassis region surrounding the core region, said chassis region comprising front, back and waist regions, while the core region is located at least in a crotch portion of the article, a liquid impermeable backsheet is arranged at least in the core region on the garment facing side of the absorbent core and a liquid permeable topsheet is arranged at least in the core region on the wearer facing side of the absorbent core.

BACKGROUND

Absorbent articles having defined core regions and chassis regions are supposed to have a comfortable fit about the wearer. For pant articles like pant diapers, sanitary pants and incontinence pants it is also desirable that the articles are capable of being pulled up and down over the hips of the wearer to allow the wearer or caregiver to easily put on and remove the article when it has been soiled. It is thus known to make such absorbent pants with elasticized stretchable side panels and waist portion, usually comprising elastic members, such as elastic threads, contractably affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one film sheet laminated to a necked film. Both films may be non-elastic. The films may further be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and after that stretch the composite material causing the non-elastic materials to break. The elastic film material may be of a breathable material. The laminate may be incorporated in an absorbent article.

Further examples of absorbent articles which in part are made of elastic laminates are found in U.S. Pat. No. 6,476,289 and JP 10043235.

There is however still room for improvement with respect to comfort, fit and cloth-like feel of absorbent articles of the above mentioned type.

SUMMARY

One of the objects of the present invention is to provide an absorbent article having a core region and a chassis region and which combines properties of comfort and fit to the wearer's body and a soft and cloth-like feeling close to textile materials. These and further objects have been accomplished by the fact that said article at least in part of the chassis region comprises an outer coversheet in the form of an elastic laminate having a Softness (S) according to Kawabata of at least 20, wherein the laminate is comprised of first and second layers of fibrous material and an elastic film layer located between said first and second fibrous layers.

Preferably the elastic laminate has a Softness (S) according to Kawabata of at least 30 and more preferably at least 40.

According to one aspect of a preferred embodiment of the invention, the elastic laminate has a Formability (F) according to Kawabata of no more than 50, preferably no more than 30, more preferably no more than 20 and most preferably no more than 10.

In one embodiment, the elastic laminate has a Drapability (D) according to Kawabata of no more than 40.

In a further embodiment the elastic film layer is breathable.

In one aspect of a preferred embodiment of the invention, the elastic laminate has a Water Vapour Transmission Rate according to ASTM E96-00 Procedure D of at least 1500 g/m² 24 h and preferably at least 3000 g/m² 24 h.

According to a further embodiment a substantial part of the crotch portion of the article is free from said elastic laminate.

According to one aspect of a further embodiment of the invention, said elastic laminate is arranged in at least a substantial part of the front region of the chassis, which in use is intended to be applied over the stomach of the wearer.

According to a further aspect, the surface area of the absorbent core amounts to no more than 30%, preferably no more than 20% of the total surface area of the article as measured in a flat state as shown in FIG. 2.

According to a further embodiment, said elastic laminate has an elasticity in the transverse direction of the article of at least 30%, preferably at least 50% and more preferably at least 70%, when measured according to the elasticity test specified in the description.

For certain applications it is preferred that the waist region of the chassis region is free from said elastic laminate.

In one embodiment of the invention the elastic laminate constitutes both the outer and an inner coversheet of the article in at least a part of the chassis region.

In a further aspect, the article is a pull-up pant product comprising an elastic waist region, which is free from said elastic laminate, a crotch portion which is also free from said elastic laminate and wherein the elastic laminate is arranged in at least a substantial part of the front region of the chassis, which in use is intended to be applied over the stomach of the wearer.

According to one embodiment said elastic laminate comprises first and second fibrous layers of spunbond material, each having a basis weight of between 10 and 35 g/m², preferably between 12 and 30 g/m², more preferably between 15 and 25 g/m², and a breathable elastic film layer having a basis weight between 20 and 100 g/m², preferably between 20 and 60 g/m².

BRIEF DESCRIPTION OF THE DRAWING FIGURES

DETAILED DESCRIPTION OF PREFERRED EMBODIMENTS

Figure 1:
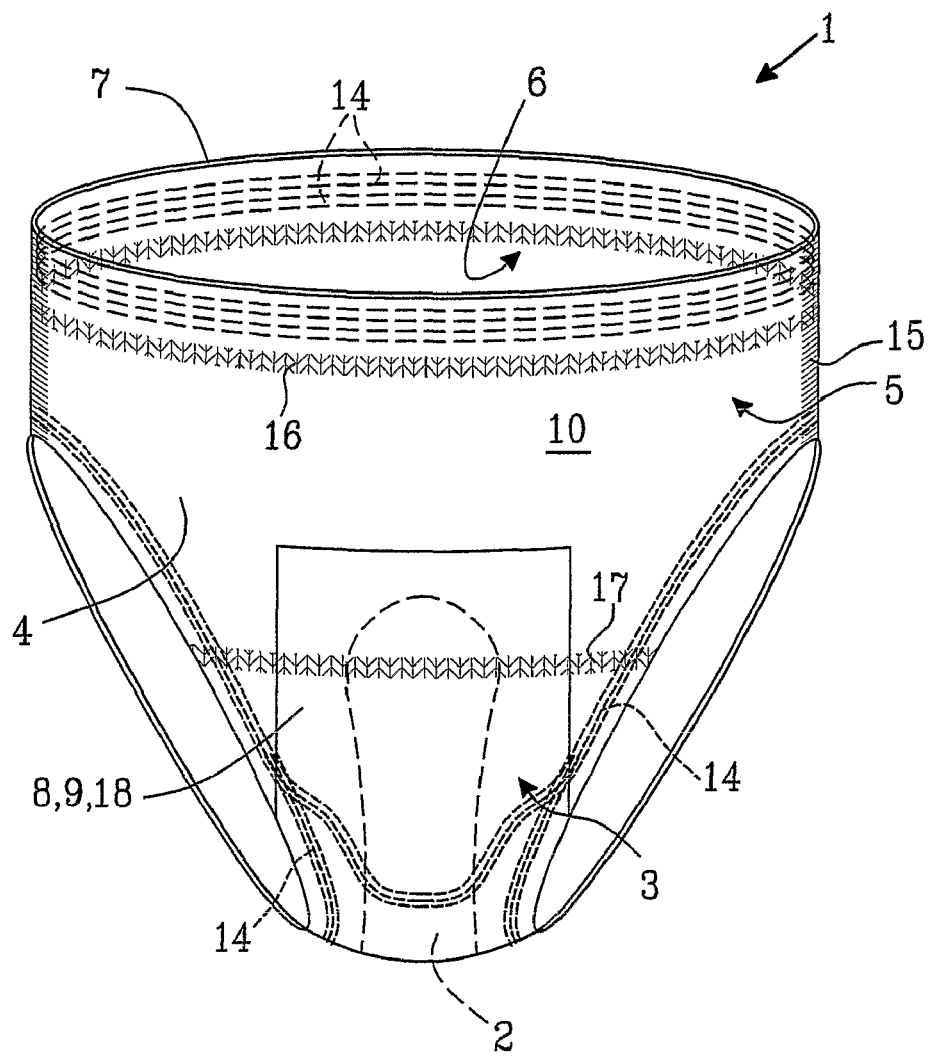
FIG. 1 shows a perspective view of an embodiment of a pant diaper.

The invention is described in further detail below, with reference to the preferred embodiments shown in the accompanying drawings.

Absorbent Article

The term "absorbent article" refers to products that are placed against the skin of the wearer to absorb and contain body exudates, like urine, faeces and menstrual fluid. The preferred embodiments of the invention mainly refer to disposable absorbent articles, which means articles that are not intended to be laundered or otherwise restored or reused as an absorbent article after use. In addition, pant type absorbent articles are referred to having a core region and a chassis region surrounding the core region. Examples of such pant type absorbent articles are pant diapers, sanitary pants and incontinence pants.

The drawings show an embodiment of a pant diaper 1 for an infant or an incontinent adult. Said pant diaper typically comprises an absorbent core 2 located in a core region 3 of the article, and a chassis region 4 surrounding the core region. The chassis region comprises front 5, back 6 and waist regions 7. The core region 3 is located in the crotch portion (a) of the article and extends a certain distance into the front 5 and back regions 6. The crotch portion (a) is herewith defined as the narrow part of the article intended to be worn in the wearer's crotch between the legs. The article has a longitudinal direction y and a transverse direction x.

The article comprises a liquid permeable topsheet 8 and a liquid impermeable backsheet 9 covering the core region 3. The absorbent core 2 is enclosed between the topsheet and the backsheet.

The liquid permeable topsheet 8 preferably comprises a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be penetrated by body fluid, e g urine or menstrual fluid. The topsheet may further be different in different parts of the absorbent article.

The liquid impervious backsheet 9 covering the core region 3 on the garment facing side of the core, is preferably a liquid impervious material, such as a thin plastic film, e.g. a polyethylene or polypropylene film, a nonwoven material coated with a liquid impervious material, a hydrophobic nonwoven material, which resists liquid penetration or laminates of plastic films and nonwoven materials. The core region backsheet material 9 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 9 is also preferably inelastic.

The outer coversheet 10 covering the front and rear parts 5 and 6 of the chassis region 4 comprises an elastic laminate 11. The laminate 11 is elastic at least in the transverse x-direction of the article. The elasticity in the x-direction should be at least 30%, preferably at least 50% and more preferably at least 70%, as measured by the elasticity test specified below.

The elastic laminate 11 includes first and second outer layers of fibrous material 12a and 12b and a middle elastic film layer 13 located between said fibrous layers. The outer fibrous layers 12a and 12b are chosen to provide a soft and cloth-like feel to the laminate. Examples of suitable materials are carded webs and spunbond materials. The basis weight of the fibrous material layers should be between 10 and 35 $g/m^2$, preferably between 12 and 30 $g/m^2$, more preferably between 15 and 25 $g/m^2$. Examples of suitable polymers used in the fibrous materials are polyethylene, polypropylene and other polyolefin homopolymers and copolymers, polyester. Natural fibers, for example cotton, may also be used as long as they provide the required soft and cloth-like feel.

The middle layer 13 is according to one embodiment of the invention an apertured elastic film having a basis weight between 20 and 100 $g/m^2$, preferably between 20 and 60 $g/m^2$. The film may be of any suitable elastic polymer, natural or synthetic. Some examples of suitable materials for the elastic film are low crystallinity polyethylenes, metallocene catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The laminate 11 may be manufactured according to a modified version of the method disclosed in WO 03/047488, wherein one nonwoven layer 12a is applied to the film 13 in a tacky state and will thus bond to the film layer, while the other nonwoven layer 12b is adhesively laminated to the film layer 13 using for example a pressure sensitive hot melt adhesive. The modification lies in that the laminate is incrementally stretched to a point below the elongation at peak load of at least one of the non-elastic nonwoven layers to remain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break and are thereby completely torn. Therefore, as described in WO 03/047488, the elongation of the laminate is not limited by the stretch modulus of the non-elastic material.

In contrast to the method described in WO 03/047488, upon manufacture of a laminate according to the present invention, at least one, preferably both fibrous layers which are bound to the elastic film are not completely torn. Selection of fibrous materials which have an elongation at maximum load greater than the elongation at break of the elastic laminate allows the elastic film to stretch during use without being hindered by the fibrous layers.

The basis weights of the individual layers of the laminate referred to above relate to the basis weight in the laminate after stretching.

It is preferred that the elastic laminate 10 has a breathability (Water Vapour Transmission Rate) according to ASTM E96-00 Procedure D of at least 1500, preferably at least 3000 $g/m^2$ 24 h.

The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent core may be varied to be suited for different uses such as for infants or for adult incontinent persons.

The pant diaper disclosed in FIG. 1 is intended to enclose the lower part of the wearer's trunk like a pair of absorbent pants. It comprises a core region 3 located in the crotch portion a of the article and extending into the front and back regions of the absorbent pants. A chassis region 4 surrounds the core region 3. The core region 3 is defined as the surface area of the article which is occupied by the absorbent core 2 and the areas outside the core which are covered by the liquid-impervious backsheet 9. The chassis region comprises front 5, back 6 and waist regions 7. The front 5 and back regions 6 are joined to each other along their longitudinal edges by ultrasonic welds 15, glue strings or the like.

Figure 2:
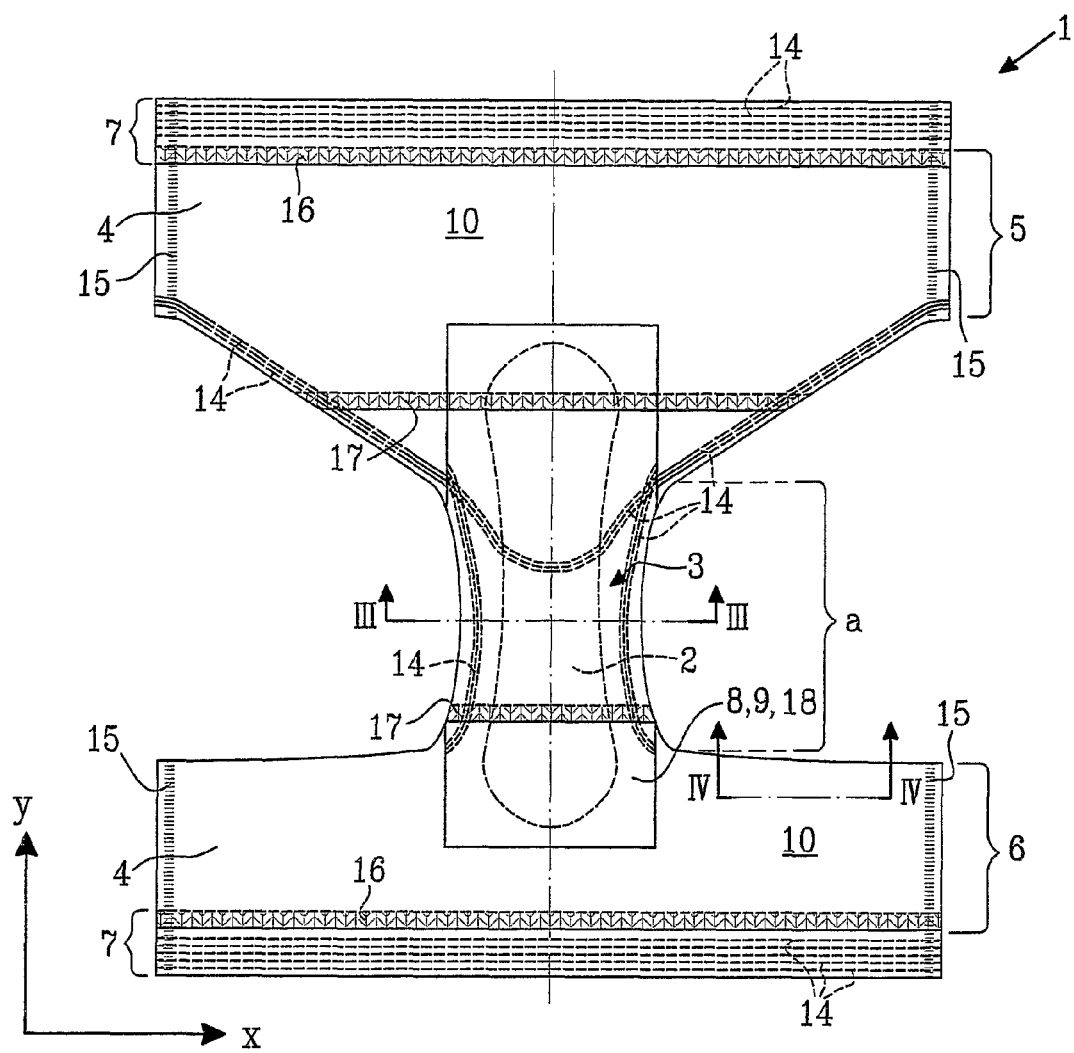
FIG. 2 is a simplified plan view of the pant diaper in its flat, uncontracted state prior to formation.
Figure 3:
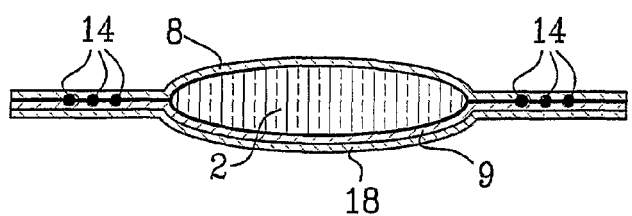
FIG. 3 is a cross section according to the line III-III in FIG. 2.
Figure 4:
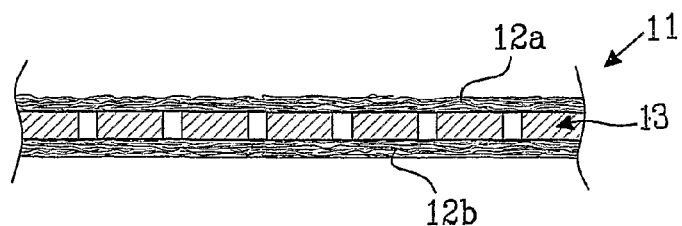
FIG. 4 is a cross section through an elastic laminate according to an embodiment of the invention.

According to one embodiment of the invention the surface area of the absorbent core 2 amounts to no more than 30% of the total surface area of the article, preferably no more than 20% as measured during flat state of the article as shown in FIG. 2.

The elastic laminate 11 may cover the entire article, including the core region 3 and the entire chassis region 4. However according to a preferred embodiment a substantial part of the crotch portion of the article is free from the elastic laminate 11. A "substantial part" used herein refers to at least 50%, preferably at least 75%. Preferably also the waist region 7 of the chassis region is free from the elastic laminate 11. The waist region 7 comprises a nonwoven material that is elasticized by elastic members 14, such as elastic threads, contractably affixed between material layers, such as nonwoven materials. Such elastic members 14 may also be arranged around the leg openings of the article. Ultrasonic welds 16, glue strings or the like, join the elastic laminate 11 to the elasticized nonwoven in the waist region 7.

The liquid-impervious backsheet material 9 underlies the absorbent core 2 and adjacent areas of the chassis region immediately outside the absorbent core 2. The area covered by the liquid-impervious backsheet 9 is defined as the core region 3. A nonwoven material 18 is arranged on the garment facing side of the liquid-impervious backsheet 9 in the crotch portion of the article. The nonwoven material 18 is joined to the elastic laminate 11 by means of ultrasonic welds 17, glue strings or the like. The elastic laminate 11 and the liquid impervious backsheet overlap in the outer parts of the core region 3, as seen in FIG. 2, wherein the elastic laminate 11 is arranged on the garment facing side of the liquid impervious backsheet 9.

The elastic laminate 11 is preferably arranged as an outside coversheet material over a substantial part of the chassis region, except for the waist region 7. It is preferred that the elastic laminate is arranged at least over a substantial part of the front region 5 of the chassis region 4, which during use is intended to be applied against the stomach of the wearer. A "substantial part" used herein means at least 50% of the surface area, preferably at least 75% and most preferably at least 90% of the surface area of the front region 5 of the chassis. The elastic laminate 11 preferably also constitutes an inner coversheet of the article in said portions of the chassis region. Thus no additional topsheet material is required in these parts of the article.

No additional elasticized side panels joining the front and back regions 5 and 6 are needed when using the elastic laminate 11. However, if desired, additional elasticized side panels may of course be provided, especially in cases where the elastic laminate 11 is arranged only in parts of the front and/or back regions.

The elastic laminate should have a Softness (S) according to Kawabata of at least 20, preferably at least 30 and most preferably at least 40.

It is further desired that it has a Formability (F) according to Kawabata of no more than 50, preferably no more than 30, more preferably no more than 20 and most preferably no more than 10.

It is also desired that the elastic laminate has a Drapability (D) shape to Kawabata of no more than 40.

Description of Test Methods

Elasticity Test Method

The Elasticity Test Method measures how an elastic material behaves at repeated load and unload cycles. According to the Elasticity Test Method, the sample is stretched to a predetermined elongation and a cyclic movement between 0 and said predetermined elongation is performed. Desired load and unload forces are recorded. The permanent, i.e. remaining, elongation of the relaxed material is measured.

A tensile tester, preferably a Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the specific apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centered and fastened perpendicularly in the clamps. The tensile tester is started and three cycles between 0 and the predetermined elongation, equal to the highest defined $1^{st}$ load, are performed. Before the last cycle the sample is relaxed for 1 minute, then the permanent elongation is measured by stretching the sample until a force of 0.1 N is detected and the elongation is read.

The permanent elongation after relaxation is preferably less than 10% when it is measured by the method above. Thus, using said Elasticity Test Method defined herein, an elasticity of 30% is characterized as the laminate preferably having a permanent relaxation after elongation of less than 10% after being exerted to an elongation of 30% in the tensile tester above. An elongation of 30% means an elongation to a length that is 30% longer than the initial length of the sample.

Kawabata Test

The Kawabata KES-FB test is a Japanese quality judgment system for used for textile materials and is disclosed in "The Standardization and Analysis of Hand Evaluation (2nd Edition), Sueo Kawabata, July 1980, The Hand Evaluation and Standardization Committee, The Textile Machinery Society of Japan". The test used in this invention uses two of the Kawabata testing machines, KES-FB2 for measuring Bending rigidity, B ($gfcm^2/cm$), and KES-FB1 for measuring Shear stiffness, G (gf/cm·degree) and Tensile strain, EMT (%).

Bending Rigidity (B) KES-FB2

The slope was measured between 0.5 $cm^{-1}$ and 1.5 $cm^{-1}$ and −0.5 $cm^{-1}$ and −1.5 $cm^{-1}$.

The measurements were performed in both directions (machine direction, MD, and cross direction, CD) with the following settings:
Total sample area: 20×20 cm;
Maximum curvature: Kmax=±2.5 cm$^{-1}$;
Bending rate: 0.5 cm$^{-1}$/sec;
Sample effective dimension: 20 cm length and 1 cm width;
Bending deformation is applied to the width direction.
Shear Stiffness (G) KES-FB1

The slope was measured between 0.5 cm$^{-1}$ and 2.5 cm$^{-1}$ and −0.5 cm$^{-1}$ and −2.5 cm$^{-1}$.

The measurements were performed in both directions (MD and CD) with the following settings:
Total sample area: 20×20 cm;
Tension of specimen: W=W=10 gf/cm;
Maximum shear angle: φ=±8°.
Sample effective dimension: 20 cm width and 5 cm length;
Shear deformation is applied to the width direction.
Tensile Strain (EMT)

The measurements were performed in both directions (MD and CD) with the following settings:
Total sample area: 20×20 cm;
Maximum load: Fm=500 gf/cm;
Tensile speed: 0.2 mm/sec.
Sample effective dimension: 20 cm width and 2.5 cm length;
Tensile deformation is applied to the length direction.
Elongation sens 50 mm/10V.
Softness (S)

The Softness (S) according to Kawabata is obtained from the formula:

$$S=\sqrt{EMT/B}$$

Formability (F)

The Formability (F) according to Kawabata is obtained from the formula:

$$F=B \cdot EMT.$$

Drapability (D)

The Drapability (D) according to Kawabata is obtained from the formula:

$$D=116+25 \cdot \log(B \cdot G/W),$$ wherein $W$ is the basis weight of the sample.

Example

Four different samples were measured in a Kawabata test with respect to Bending rigidity (B), Shear stiffness (G) and Tensile strain (EMT). From these measured values the Softness (S), Formability (F) and Drapability (D) were calculated. The four samples were:

Sample laminate (SL): an elastomeric laminate according to the invention comprising an inner apertured three-layer elastomeric film of PE-SEBS-PE, basis weight 36 g/m$^2$ and two outer layers of spunbond material, PP (polypropylene), each having a basis weight of 22 g/m$^2$. The laminate is produced by a modified version of the method disclosed in WO 03/04788, wherein one spunbond layer is applied to the film in a tacky state and will thus bond to the film layer, while the other spunbond layer is adhesively laminated to the film layer using for example a pressure sensitive hot melt adhesive (glue amount 3 g/m$^2$). The laminate is incrementally stretched, at which the non-elastic spunbond layers are stretched to a point below the elongation at peak load to retain some strength in the spunbond layers.

The above mentioned basis weights of the layers refers to the finished laminate after stretching. Before stretching the basis weight of the individual layers were: inner film layer 40 g/m$^2$, outer spunbond layers 25 g/m$^2$ each and glue layer 3 g/m$^2$. Since it is difficult to measure the basis weights of the individual layers after lamination and stretching an approximation has been made from the basis weights of the layers before lamination and stretching. The laminate before stretching had a total basis weight before stretching of 93 g/m$^2$ and after stretching it had a basis weight of 85 g/m$^2$, which means a deformation of about 10%. It is then assumed that the deformation of the individual fibrous layers and the film layer is the same, i.e. about 10%.

Ref 1: Cotton-knitted goods, so called jersey with elastomeric threads.

Ref 2: Outer coversheet of Tena Discreet incontinence pant, odour control, size medium, produced by SCA Hygiene Products AB. The outer coversheet comprises two layers of nonwoven with parallel elastic threads there between, which wrinkle the material.

Ref 3: Outer coversheet material of Poïse normal super incontinence pant produced by Kimberly-Clark. The outer coversheet comprises two layers of nonwoven with parallel elastic threads there between which wrinkle the material.

A climate conditioning of the materials were performed in 20.0 and 65% RH for 48 hours. For the pant products the absorbent core was removed and the outer coversheet was stretched over a knitwear measuring device for 24 hours and was then allowed to relax in the same climate during 24 hours.

The sizes of the samples were 10×10 cm.

All tests were made on three samples and in two material directions (machine direction, MD, and cross direction, CD).

The following results were obtained.

TABLE 1

| Sample | B, Bending rigidity (gf · cm$^2$/cm) | | | G, Shear stiffness (gf/cm · degree) | | | EMT, Tensile strain (%) | | |
|---|---|---|---|---|---|---|---|---|---|
| | MD | CD | Mean | MD | CD | Mean | MD | CD | Mean |
| SL | 0.095 | 0.022 | 0.059 | 1.46 | 1.38 | 1.42 | 208.4 | 92.0 | 150.2 |
| Ref. 1 | 0.03 | 0.03 | 0.03 | 0.58 | 0.64 | 0.61 | 160.6 | 173.2 | 166.9 |
| Ref. 2 | 1.05 | 0.09 | 0.57 | 0.87 | 0.68 | 0.77 | 23.9 | 211.7 | 117.8 |
| Ref. 3 | 1.53 | 0.04 | 0.78 | 1.74 | 1.21 | 1.47 | 26.28 | 195.3 | 110.8 |

From these results the Softness (S), the Drapability (D) and the Formability (F) according to Kawabata were calculated according to the formulas stated above. These results are stated in Table 2 below.

TABLE 2

| Sample | Softness (S) $\sqrt{EMT/B}$ | Drapability (D) $116 + 25 \log(B \cdot G/W)$ | Formability (F) $B \cdot EMT$ | Basis Weight (W) g/m$^2$ |
|---|---|---|---|---|
| SL | 50 | 40 | 9 | 88 |
| Ref. 1 | 75 | 13 | 5 | 231 |
| Ref. 2 | 14 | 45 | 67 | 160 |
| Ref. 3 | 12 | 51 | 87 | 133 |

The results should be interpreted in the following way:
Softness (S): a higher value indicates a softer material.
Drapability (D): a higher value indicates a stiffer material.
Formability (F): a higher value indicates that the material is less formable.

The test laminate according to the preferred embodiments of invention has a Softness (S) and a Formability (F) according to Kawabata which is close to cotton-knitted goods (Ref. 1). Also the Drapability (D) according to Kawabata is closer to the cotton-knitted reference material than other two tested materials, used as outer coversheets on conventional incontinence pants. Thus the use of the elastomeric laminate as outer coversheet material in at least a part of the chassis region of the absorbent pant provides a pant article having a cloth-like feeling close to a cotton material. The pant will also have an excellent comfort and fit to the wearer's body. By using the elastomeric laminate only in those part of the pant in which the properties of the material is best utilized, a very economic utilization of the material is accomplished

The invention claimed is:

1. A pant absorbent article, said article having a core region comprising an absorbent core and a chassis region surrounding the core region, said chassis region comprising front, back and waist regions, while the core region is located at least in a crotch portion of the article, a liquid impermeable backsheet is arranged at least in the core region on the garment facing side of the absorbent core and a liquid permeable topsheet is arranged at least in the core region on the wearer facing side of the absorbent core, said article having a longitudinal direction and a transverse direction, wherein said article at least in part of the chassis region comprises an outer coversheet in the form of an elastic laminate, said elastic laminate being arranged in at least a substantial part of the front region of the chassis, which is adapted to be applied over the stomach of the wearer, said elastic laminate is composed of first and second layers of fibrous material and an elastic film layer located between said first and second fibrous layers, wherein the elastic laminate is obtained by: (i) bonding a first layer of fibrous material to the film layer by applying the first layer to the film layer without adhesive while the first layer is in an unstretched state and the film layer is in a tacky state, and (ii) adhesively laminating a second layer of fibrous material to the film layer, wherein said elastic laminate has a softness according to Kawabata of at least 20.

2. The absorbent article as claimed in claim 1, wherein said elastic laminate has a Softness according to Kawabata of at least 30.

3. The absorbent article as claimed in claim 2, wherein the Softness is at least 40.

4. The absorbent article as claimed in claim 1, wherein said elastic laminate has a Formability according to Kawabata of no more than 50.

5. The absorbent article as claimed in claim 4, wherein said elastic laminate has a Formability according to Kawabata of no more than 30.

6. The absorbent article as claimed in claim 5, wherein the Formability is no more than 20.

7. The absorbent article as claimed in claim 5, wherein the Formability is no more than 10.

8. The absorbent article as claimed in claim 1, wherein said elastic laminate has a Drapability according to Kawabata of no more than 40.

9. The absorbent article as claimed in claim 1, wherein said elastic film layer is breathable.

10. The absorbent article as claimed in claim 9, wherein said elastic laminate has a Water Vapour Transmission Rate according to ASTM E96-00 Procedure D of at least 1500 $g/m^2$ 24 h.

11. The absorbent article as claimed in claim 10, wherein the Water Vapour Transmission Rate is at least 3000 $g/m^2$ 24 h.

12. The absorbent article as claimed in claim 1, wherein said elastic laminate has an elasticity in the transverse direction of the article of at least 30% when measured after stretching said elastic laminate to a predetermined elongation and performing a cyclic movement between 0 and said predetermined elongation.

13. The absorbent article as claimed in claim 12, wherein the elasticity is at least 50%.

14. The absorbent article as claimed in claim 12, wherein the elasticity is at least 70%.

15. The absorbent article as claimed in claim 1, wherein a substantial part of the crotch portion of the article is free from said elastic laminate.

16. The absorbent article as claimed in claim 15, wherein the waist region of the chassis region is free from said elastic laminate.

17. The absorbent article as claimed in claim 15, wherein said elastic laminate is arranged in at least a substantial part of the front region of the chassis, which in use is intended to be applied over the stomach of the wearer.

18. The absorbent article as claimed in claim 1, wherein the surface area of the absorbent core amounts to no more than 30% of the total surface area of the article as measured in a flat state of the article.

19. The absorbent article as claimed in claim 1, wherein the article is a pull-up pant product comprising an elasticized waist region, which is free from said elastic laminate, a crotch portion which is also free from said elastic laminate and wherein the elastic laminate is arranged in at least a substantial part of the front region of the chassis, which in use is intended to be applied over the stomach of the wearer.

20. The absorbent article as claimed in claim 1, wherein the first and second fibrous layers are of spunbond material, each having a basis weight of between 10 and 35 $g/m^2$ and the elastic film layer is breathable and having a basis weight between 20 and 100 $g/m^2$, said elastic laminate having a Water Vapour Transmission Rate according to ASTM E96-00 Procedure D of at least 1500 $g/m^2$ 24 h.

21. The absorbent article as claimed in claim 1, wherein the absorbent article is a pant diaper, a sanitary pant or an incontinence pant.

22. The absorbent article as claimed in claim 1, wherein the first and second fibrous layers are of spunbond material, each having a basis weight of between 11 and 30 $g/m^2$ and the elastic film layer is breathable and having a basis weight between 20 and 60 $g/m^2$, said elastic laminate having a Water Vapour Transmission Rate according to ASTM E96-00 Procedure D of at least 3000 $g/m^2$ 24 h.

23. The absorbent article as claimed in claim 1, wherein at least one of the first and second fibrous layers is made of a fibrous material having an elongation at maximum load greater than the elongation at break of the elastic laminate.

24. A pant absorbent article, said article having a core region comprising an absorbent core and a chassis region surrounding the core region, said chassis region comprising front, back and waist regions, while the core region is located at least in a crotch portion of the article, a liquid impermeable backsheet is arranged at least in the core region on the garment facing side of the absorbent core and a liquid permeable topsheet is arranged at least in the core region on the wearer facing side of the absorbent core, said article having a longitudinal direction and a transverse direction, wherein said article at least in part of the chassis region comprises an outer coversheet in the form of an elastic laminate, said elastic laminate being arranged in at least a substantial part of the front region of the chassis, which is adapted to be applied over the stomach of the wearer, said elastic laminate is composed of first and second layers of fibrous material and an elastic film layer located between said first and second fibrous layers, wherein the elastic laminate is obtained by: (i) bonding a first layer of fibrous material to the film layer by applying the first layer to the film layer without adhesive while the first layer is in an unstretched state and the film layer is in a tacky state, (ii) adhesively laminating a second layer of fibrous material to the film layer, and (iii) incrementally stretching the laminated obtained after (i) and (ii) to a point below the elongation at peak load of the fibrous layers so that the fibrous layers are partially torn, wherein said elastic laminate has a softness according to Kawabata of at least 20.

\* \* \* \* \*